US007928223B2

(12) United States Patent
Lerestif et al.

(10) Patent No.: US 7,928,223 B2
(45) Date of Patent: Apr. 19, 2011

(54) PROCESS FOR THE SYNTHESIS OF 7,8-DIMETHOXY-1,3-DIHYDRO-2H-3-BENZAZEPIN-2-ONE, AND APPLICATION IN THE SYNTHESIS OF IVABRADINE AND ADDITION SALTS THEREOF WITH A PHARMACEUTICALLY ACCEPTABLE ACID

(75) Inventors: Jean-Michel Lerestif, Yvetot (FR);
Jean-Pierre Lecouve, Le Havre (FR);
Daniel Brigot, Ste Marie des Champs (FR)

(73) Assignee: Les Laboratoires Servier, Suresnes Cedex (FR)

( * ) Notice: Subject to any disclaimer, the term of this patent is extended or adjusted under 35 U.S.C. 154(b) by 28 days.

(21) Appl. No.: 12/456,437

(22) Filed: Jun. 17, 2009

(65) Prior Publication Data
US 2009/0318682 A1 Dec. 24, 2009

(30) Foreign Application Priority Data
Jun. 20, 2008 (FR) ..................... 08 03452

(51) Int. Cl.
*C07D 223/16* (2006.01)
(52) U.S. Cl. ........................................ 540/523
(58) Field of Classification Search .......... 540/523
See application file for complete search history.

(56) References Cited

U.S. PATENT DOCUMENTS

| 4,490,369 A | * | 12/1984 | Reiffen et al. | 514/212.07 |
| 4,584,293 A | * | 4/1986 | Reiffen et al. | 514/212.06 |
| 4,604,389 A | * | 8/1986 | Reiffen et al. | 514/212.07 |
| 4,616,011 A | * | 10/1986 | Reiffen et al. | 514/221 |
| 4,737,495 A | * | 4/1988 | Bomhard et al. | 514/212.07 |

FOREIGN PATENT DOCUMENTS

| EP | 0161604 | 11/1985 |
| EP | 0534859 | 3/1993 |
| WO | 2005/110993 | 11/2005 |
| WO | 2007/011820 | 1/2007 |

OTHER PUBLICATIONS

Bomhard, A., et al., "Specific bradycardics agents. 2. heteroaromatic modification in the side chain of specific bradycardics benzazepinones: chemistry, pharmacology and structure-activity relationships" Journal of Medicinal Chemistry, vol. 34, p. 942-947, Jan. 1991.
Reffen, M., et al., "Specific Bradycardic agents. 1. chemistry, pharmacology and structure-activity relationships of substituted benzazepinones, a new clas of compounds exerting antiischemic properties" Journal of Medicinal Chemistry, vol. 33, No. 5, p. 1497-1504, May 1, 1990.
French Preliminary Search Report for FR0803452 of Feb. 19, 2009.
March, J.; *Advanced Organic Chemistry, Fourth Edition*, 1992, 400-401 and 437-438.

\* cited by examiner

*Primary Examiner* — Bruck Kifle
(74) *Attorney, Agent, or Firm* — Hueschen and Sage

(57) ABSTRACT

Process for the synthesis of the compound of formula (I):

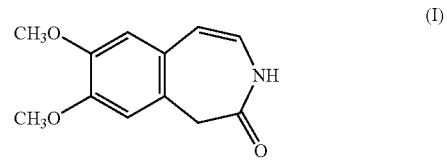

Application in the synthesis of ivabradine, addition salts thereof with a pharmaceutically acceptable acid and hydrates thereof.

18 Claims, No Drawings

PROCESS FOR THE SYNTHESIS OF 7,8-DIMETHOXY-1,3-DIHYDRO-2H-3-BENZAZEPIN-2-ONE, AND APPLICATION IN THE SYNTHESIS OF IVABRADINE AND ADDITION SALTS THEREOF WITH A PHARMACEUTICALLY ACCEPTABLE ACID

The present invention relates to a process for the synthesis of 7,8-dimethoxy-1,3-dihydro-2H-3-benzazepin-2-one of formula (I), and to the application thereof in the synthesis of ivabradine, addition salts thereof with a pharmaceutically acceptable acid and hydrates thereof

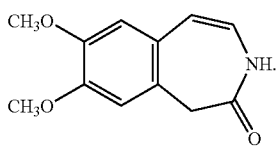

The compound of formula (I) obtained according to the process of the invention is useful in the synthesis of ivabradine of formula (II)

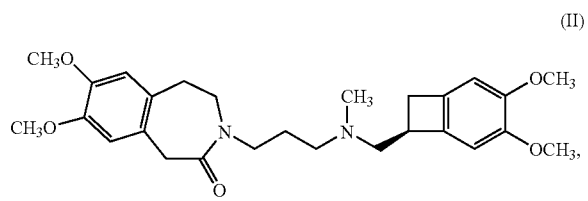

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
addition salts thereof with a pharmaceutically acceptable acid and hydrates thereof.

Ivabradine, and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and addition salts thereof with a pharmaceutically acceptable acid, and more especially its hydrochloride, have been described in the European patent specification EP 0 534 859.

That patent specification describes the synthesis of ivabradine hydrochloride starting from the compound of formula (III):

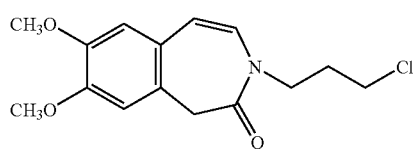

and makes reference to the publication J. Med. Chem 1990, Vol. 33(5), 1496-1504 for the preparation of that compound.

The synthesis route described in that publication for the compound of formula (III) uses an alkylation reaction on the compound of formula (I):

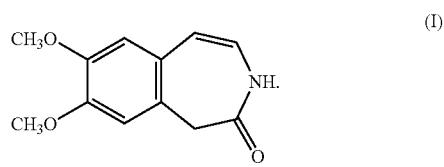

The afore-mentioned publication describes the preparation of the compound of formula (I) by using, as intermediate, N-(2,2-dimethoxyethyl)-2-(3,4-dimethoxyphenyl)acetamide obtained starting from (3,4-dimethoxyphenyl)acetic acid. Cyclisation of the phenylacetamide obtained is carried out in the presence of hydrochloric acid in acetic acid to yield the compound of formula (I) in an overall yield of 58% relative to the (3,4-dimethoxyphenyl)acetic acid.

In view of the value of ivabradine and its salts to industry, it has been imperative to find an effective process that especially makes it possible to obtain 7,8-dimethoxy-1,3-dihydro-2H-3-benzazepin-2-one of formula (I) in an excellent yield.

The Applicant has now found, surprisingly, that by using specific operating conditions it is possible to obtain the compound of formula (I) on an industrial scale in a yield greater than 92% and with a chemical purity greater than 99.5%.

More specifically, the present invention relates to a process for the synthesis of the compound of formula (I):

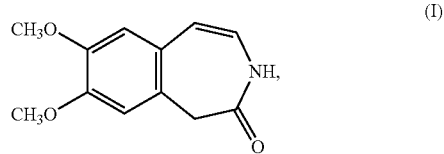

characterised in that (3,4-dimethoxyphenyl)acetic acid of formula (IV):

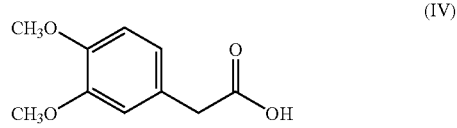

is converted into the compound of formula (V):

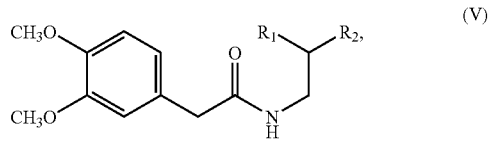

wherein the groups $R_1$ and $R_2$, which may be the same or different, represent linear or branched ($C_1$—$C_6$)alkoxy groups or, together with the carbon atom carrying them, form a 1,3-dioxane, 1,3-dioxolane or 1,3-dioxepane ring,
which is subjected to a cyclisation reaction in an acid medium to yield, after isolation, the compound of formula (I).

In one of the preferred embodiments of the invention, the conversion of the compound of formula (IV) into the compound of formula (V) is carried out by means of preliminary conversion of the compound of formula (IV) into the compound of formula (VI):

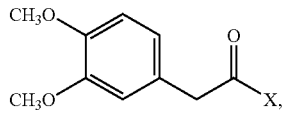
(VI)

wherein X represents a halogen atom or a group OCOR$_3$
wherein R$_3$ is a linear or branched (C$_1$—C$_6$)alkyl group, a phenyl group, a benzyl group or an imidazole group, in an organic solvent, and then the compound of formula (VI) is subjected to a condensation reaction with a compound of formula (VII):

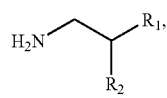
(VII)

wherein the groups R$_1$ and R$_2$, which may be the same or different, represent linear or branched (C$_1$—C$_6$)alkoxy groups or, together with the carbon atom carrying them, form a 1,3-dioxane, 1,3-dioxolane or 1,3-dioxepane ring, in the presence of a base in an organic solvent, to yield the compound of formula (V):

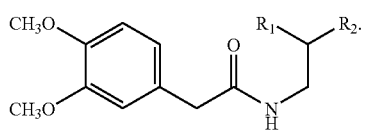
(V)

In another preferred embodiment of the invention, the conversion of the compound of formula (IV) into the compound of formula (V) is carried out by reaction with a compound of formula (VII):

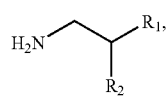
(VII)

wherein the groups R$_1$ and R$_2$, which may be the same or different, represent linear or branched (C$_1$—C$_6$)alkoxy groups or, together with the carbon atom carrying them, form a 1,3-dioxane, 1,3-dioxolane or 1,3-dioxepane ring, in the presence of a coupling agent in an organic solvent, to yield the compound of formula (V):

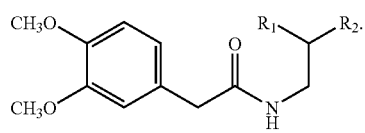
(V)

Among the coupling agents that may be used for the condensation reaction of the compound of formula (VII) with the compound of formula (IV), there may be mentioned, without implying any limitation, the following reagents or pairs of reagents: EDCI, EDCI/HOBT, EDCI/HOAT, EDCI/NHS, DCC, DCC/HOBT, DCC/HOAT, DCC/NHS, HATU, HBTU, TBTU, BOP, PyBOP, CDI, T3P.

Among the organic solvents that may be used for the condensation reaction of the compound of formula (VII) with the compound of formula (IV) in the presence of a coupling agent, there may be mentioned, without implying any limitation, toluene, dichloromethane, 2-methyltetrahydrofuran, chlorobenzene, 1,2-dichloroethane, chloroform and dioxane.

In one of the preferred embodiments of the invention, the compound of formula (V) is not isolated.

In one of the preferred embodiments of the invention, the compound of formula (VI) is not isolated.

The group X in the compound of formula (VI) preferably represents a chlorine atom.

Among the organic solvents that may be used for the reaction for conversion of the compound of formula (IV) into the compound of formula (VI), there may be mentioned, without implying any limitation, toluene, dichloromethane, 2-methyltetrahydrofuran, chlorobenzene, 1,2-dichloroethane, chloroform and dioxane.

The preferred organic solvent for the reaction for conversion of the compound of formula (IV) into the compound of formula (VI) is dichloromethane.

The temperature of the reaction for conversion of the compound of formula (IV) into the compound of formula (VI) is preferably from 20 to 40° C.

The reagent preferably used for carrying out conversion of the compound of formula (IV) into the compound of formula (VI) wherein X represents a chlorine atom is thionyl chloride.

The amount of thionyl chloride used in the reaction for conversion of the compound of formula (IV) into the compound of formula (VI) is preferably from 1 to 1.3 moles per mole of compound of formula (IV).

Among the organic solvents that may be used for the reaction between the compound of formula (VI) and the compound of formula (VII), there may be mentioned, without implying any limitation, toluene, dichloromethane, 2-methyltetrahydrofuran, chlorobenzene, 1,2-dichloroethane, chloroform and dioxane.

The preferred organic solvent for the reaction between the compound of formula (VI) and the compound of formula (VII) is dichloromethane.

The temperature of the reaction between the compound of formula (VI) and the compound of formula (VII) is preferably from 0 to 40° C.

The amount of compound of formula (VII) used in the reaction with the compound of formula (VI) is preferably from 1 to 1.2 moles per mole of compound of formula (VI).

The amount of base used in the reaction between the compound of formula (VI) and the compound of formula (VII) is preferably from 1 to 1.3 moles per mole of compound of formula (VI).

Among the bases that may be used for the reaction between the compound of formula (VI) and the compound of formula (VII), there may be mentioned, without implying any limitation, pyridine, DMAP and tertiary amines, for example triethylamine, DIEA, N-methylpiperidine, DBU, DABCO, DBN and N-methylmorpholine.

The base preferably used for the reaction between the compound of formula (VI) and the compound of formula (VII) is triethylamine.

Among the acids that may be used to carry out cyclisation of the compound of formula (V) to form the compound of formula (I), there may be mentioned, without implying any limitation, concentrated sulphuric acid, polyphosphoric acid, concentrated hydrochloric acid in aqueous solution, concentrated hydrochloric acid in solution in acetic acid, concentrated hydrobromic acid in solution in acetic acid, and methanesulphonic acid.

The amount of acid used in the reaction for cyclisation of the compound of formula (V) to form the compound of formula (I) is preferably from 5 to 15 moles per mole of compound of formula (V).

The temperature of the reaction for cyclisation of the compound of formula (V) in an acid medium is preferably from 0 to 40° C.

The acid preferably used for carrying out cyclisation of the compound of formula (V) to form the compound of formula (I) is concentrated sulphuric acid.

When the reaction intermediates are not isolated in the course of the process, the amount of concentrated sulphuric acid used in the reaction for cyclisation of the compound of formula (V) is preferably from 1.5 to 3 millileters per gram of (3,4-dimethoxyphenyl)acetic acid of formula (IV).

The compound of formula (I) obtained according to the process of the present invention is especially useful as synthesis intermediate in the synthesis of ivabradine, addition salts thereof with a pharmaceutically acceptable acid and hydrates thereof.

By way of example, alkylation of the compound of formula (I) with a compound of formula (VIII):

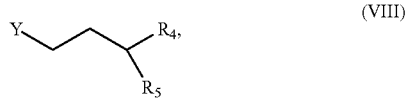

(VIII)

wherein $R_4$ and $R_5$, which may be the same or different, each represent a linear or branched $(C_1—C_6)$alkoxy group or, together with the carbon atom carrying them, form a 1,3-dioxane or 1,3-dioxolane ring, and Y represents a halogen atom, preferably a bromine atom, or a tosylate, mesylate or triflate group, yields the compound of formula (IX)

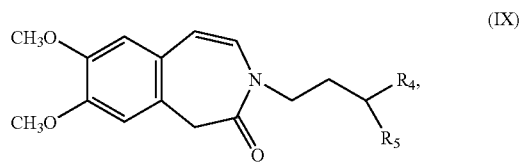

(IX)

catalytic hydrogenation of which yields the corresponding hydrogenated compound of formula (X):

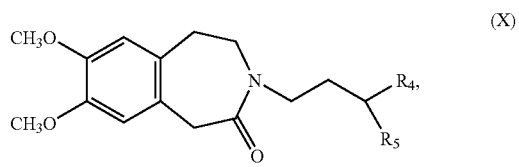

(X)

wherein $R_4$ and $R_5$ are as defined for formula (VIII), deprotection of the diacetal moiety of which yields the aldehyde of formula (XI):

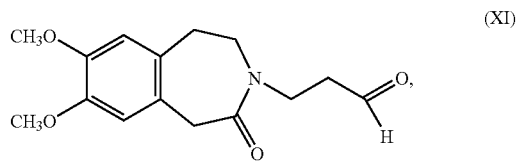

(XI)

which is reacted with (7S)-3,4-dimethoxybicyclo[4.2.0]octa-1,3,5-trien-7-yl]-N-methyl-methanamine under conditions of reductive amination to yield ivabradine, which may optionally be converted into its addition salts with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Key to the Abbreviations Used:
BOP: benzotriazol-1-yl-oxy-tris(dimethylamino)phosphonium hexafluorophosphate
CDI: carbonyldiimidazole
DABCO: 1,4-diazabicyclo[2.2.2]octane
DBN: 1,5-diazabicyclo[4.3.0]non-5-ene
DBU: 1,8-diazabicyclo[5.4.0]undec-7-ene
DCC: dicyclohexylcarbodiimide
DIEA: N,N-diisopropylethylamine
DMAP: 4-dimethylaminopyridine
EDCI: 1-(3-dimethylaminopropyl)-3-ethyl-carbodiimide hydrochloride
HATU: O-(7-azabenzotriazol-1-yl)-1,1,3,3-tetramethyluronium hexafluorophosphate
HBTU: O-(benzotriazol-1-yl)-1,1,3,3-tetramethyluronium hexafluorophosphate
HOAT: 1-hydroxy-7-azabenzotriazole
HOBT: 1-hydroxybenzotriazole
NHS: N-hydroxysuccinimide
NMP: N-methylpyrrolidone
PyBOP: O-(benzotriazol-1-yl)-oxytripyrrolidinophosphonium hexafluorophosphate
TBTU: O-(benzotriazol-1-yl)-1,1,3,3-tetramethyluronium tetrafluoroborate
T3P: n-propane phosphonic anhydride The Example hereinbelow illustrates the invention.

PREPARATION OF 7,8-DIMETHOXY-1,3-DIHYDRO-2H-3-BENZAZEPIN-2-ONE

Step A: 3,4-Dimethoxyphenyl)acetic acid chloride

Load into a reactor 135 g of (3,4-dimethoxyphenyl)acetic acid and 270 ml of dichloromethane and then bring the temperature of the reaction mixture to reflux and add, dropwise, 90 g of thionyl chloride. Stir the mixture at reflux for 3 hours. The solution obtained is used as such in the following Step.

Step B: N-(2, 2-dimethoxyethyl)-2-(3, 4-dimethoxyphenyl)acetamide

Load into a reactor 225 ml of dichloromethane, 44.15 g of 2,2-dimethoxyethylamine and 44.35 g of triethylamine and then cool the mixture to 10° C. and add, dropwise, 237.4 g of the solution obtained in the preceding Step (corresponding to 75 g of (3,4-dimethoxyphenyl)acetic acid) whilst maintaining the mass temperature at 10° C. Stir the mixture for 2 hours at 15° C. The solution obtained is used as such in the following Step.

Step C: 7,8-Dimethoxy-1,3-dihydro-2H-3-benzazepin-2-one

In a reactor containing the solution obtained in the preceding Step and cooled to 10° C., add 150 ml of 36N sulphuric acid, whilst maintaining the temperature below 20° C. Stir the mixture at 15-20° C. for 10 hours, then allow the reaction mixture to separate and collect the product-containing sulphuric acid phase.

The product is obtained by precipitation from a water/NMP mixture (4/1), filtration and drying, in a yield of 92.9 % relative to the (3,4-dimethoxyphenyl)acetic acid and with a chemical purity greater than 99.5%.

The invention claimed is:
1. A process for the synthesis of a compound of formula (I):

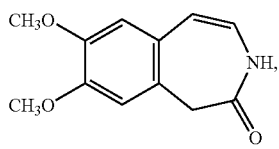

(I)

wherein (3,4-dimethoxyphenyl)acetic acid of formula (IV):

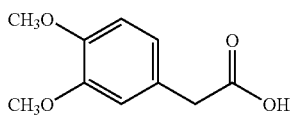

(IV)

is converted into a compound of formula (V):

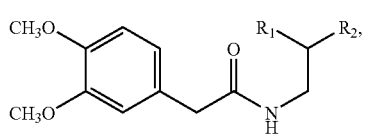

(V)

wherein $R_1$ and $R_2$, which may be the same or different, represent linear or branched ($C_1$-$C_6$) alkoxy groups or, together with the carbon atom carrying them, form a 1,3-dioxane, 1,3-dioxolane or 1,3-dioxepane ring, wherein the conversion is carried out either:
by means of preliminary conversion of the compound of formula (IV) into a compound of formula (VI):

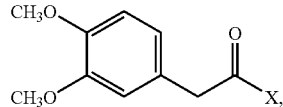

(VI)

wherein X represents a halogen atom or a $OCOR_3$ group, wherein $R_3$ is a linear or branched ($C_1$-$C_6$)alkyl group, a phenyl group, a benzyl group or an imidazolyl group,
in an organic solvent,
and the compound of formula (VI) is subjected to a condensation reaction with a compound of formula (VII):

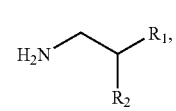

(VII)

wherein $R_1$ and $R_7$, which may be the same or different, represent linear or branched ($C_1$-$C_6$)alkoxy groups or, together with the carbon atom carrying them, form a 1,3-dioxane, 1,3-dioxolane or 1,3-dioxepane ring,
in the presence of a base in an organic solvent,
to yield the compound of formula (V):

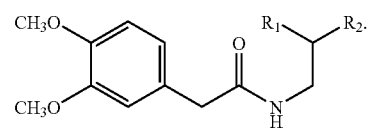

(V)

or
by reaction of the compound of formula (IV) with a compound of formula (VII):

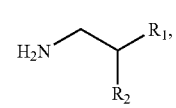

(VII)

wherein $R_1$ and $R_2$, which may be the same or different, represent linear or branched ($C_1$-$C_6$)alkoxy groups or, together with the carbon atom carrying them, form a 1,3-dioxane, 1,3-dioxolane or 1,3-dioxepane ring,
in the presence of a coupling agent in an organic solvent,
to yield the compound of formula (V):

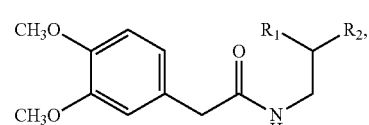

(V)

wherein the compound of formula (V) is not isolated and is directly subjected to a cyclisation reaction in an acid medium, wherein the acid medium is selected from concentrated sulphuric acid, polyphosphoric acid, concentrated hydrochloric acid in aqueous solution, concentrated hydrochloric acid in solution in acetic acid, concentrated hydrobromic acid in solution in acetic acid, and methanesulphonic acid, to yield, after isolation, the compound of formula (I).

2. The process of claim 1, wherein the compound of formula (VI) is not isolated.

3. The process of claim 1, wherein, in the compound of formula (VI), X represents a chlorine atom.

4. The process of claim 1, wherein the solvent used for conversion of the compound of formula (IV) into the compound of formula (VI) is dichloromethane.

5. The process of claim 1, wherein the temperature of the reaction for conversion of the compound of formula (IV) into the compound of formula (VI) is from 20 to 40° C.

6. The process of claim 1, wherein the reagent used for conversion of the compound of formula (IV) into the compound of formula (VI) is thionyl chloride.

7. The process of claim 6, wherein the amount of thionyl chloride used in the reaction for conversion of the compound of formula (IV) into the compound of formula (VI) is from 1 to 1.3 moles per mole of compound of formula (IV).

8. The process of claim 1, wherein the solvent for the reaction between the compounds of formulas (VI) and (VII) is dichloromethane.

9. The process of claim 1, wherein the temperature of the reaction between the compounds of formulas (VI) and (VII) is from 0 to 40° C.

10. The process of claim 1, wherein the amount of compound (VII) used in the reaction with the compound of formula (VI) is from 1 to 1.2 moles per mole of compound of formula (VI).

11. The process of claim 1, wherein the amount of base used in the reaction between the compounds of formulas (VI) and (VII) is from 1 to 1.3 moles per mole of compound of formula (VI).

12. The process of claim 1, wherein the base used in the reaction between the compounds of formulas (VI) and (VII) is pyridine, DMAP or a tertiary amine.

13. The process of claim 12, wherein the base used in the reaction between the compounds of formulas (VI) and (VII) is triethylamine.

14. The process of claim 1, wherein the amount of acid used in the reaction for cyclisation of the compound of formula (V) is from 5 to 15 moles per mole of compound of formula (V).

15. The process of claim 1, wherein the temperature of the reaction for cyclisation of the compound of formula (V) in an acid medium is from 0 to 40° C.

16. The process of claim 1, wherein the acid used for cyclisation of the compound of formula (V) is concentrated sulphuric acid.

17. The process of claim 16, wherein the amount of concentrated sulphuric acid used in the reaction for cyclisation of the compound of formula (V) is from 1.5 to 3 millilitres per gram of (3,4-dimethoxyphenyl)acetic acid of formula (IV).

18. A process for the synthesis of ivabradine and pharmaceutically acceptable salts thereof, wherein a compound of formula (IV)

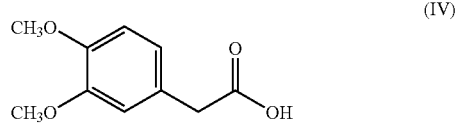

is converted into a compound of formula (V):

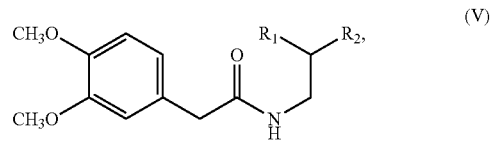

wherein $R_1$ and $R_2$, which may be the same or different, represent linear or branched $(C_1-C_6)$alkoxy groups or, together with the carbon atom carrying them, form a 1,3-dioxane, 1,3-dioxolane or 1,3-dioxepane ring, wherein the conversion is carried out either:
  by means of preliminary conversion of the compound of formula (IV) into a compound of formula (VI):

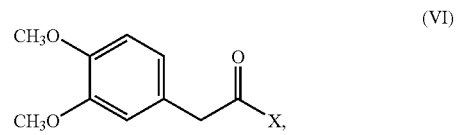

wherein X represents a halogen atom or a $OCOR_3$ group, wherein $R_3$ is a linear or branched $(C_1-C_6)$alkyl group, a phenyl group, a benzyl group or an imidazolyl group,
  in an organic solvent,
  and the compound of formula (VI) is subjected to a condensation reaction with a compound of formula (VII):

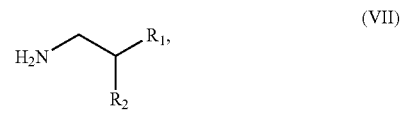

wherein $R_1$ and $R_2$, which may be the same or different, represent linear or branched $(C_1-C_6)$alkoxy groups or, together with the carbon atom carrying them, form a 1,3-dioxane, 1,3-dioxolane or 1,3-dioxepane ring,
  in the presence of a base in an organic solvent,
  to yield the compound of formula (V):

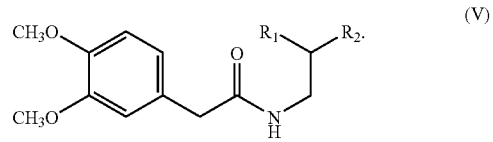

or
  by reaction of the compound of formula (IV) with a compound of formula (VII):

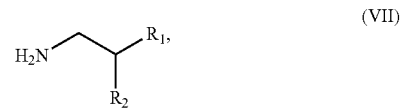

wherein $R_1$ and $R_2$, which may be the same or different, represent linear or branched ($C_1$-$C_6$)alkoxy groups or, together with the carbon atom carrying them, form a 1,3-dioxane, 1,3-dioxolane or 1,3-dioxepane ring, in the presence of a coupling agent in an organic solvent, to yield the compound of formula (V):

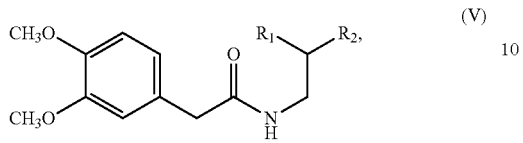

wherein the compound of formula (V) is not isolated and is directly subjected to a cyclisation reaction in an acid medium, wherein the acid medium is selected from concentrated sulphuric acid, polyphosphoric acid, concentrated hydrochloric acid in aqueous solution, concentrated hydrochloric acid in solution in acetic acid, concentrated hydrobromic acid in solution in acetic acid, and methanesulphonic acid, to yield, after isolation, the compound of formula (I):

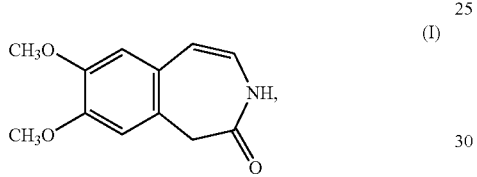

which compound of formula (I) is alkylated with a compound of formula (VIII):

wherein $R_4$ and $R_5$, which may be the same or different, each represent a linear or branched ($C_1$-$C_6$)alkoxy group or, together with the carbon atom carrying them, form a 1,3-dioxane or 1,3-dioxolane ring, and Y represents a halogen atom, preferably a bromine atom, or a tosylate, mesylate or triflate group, to yield a compound of formula (IX):

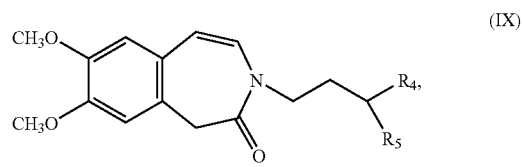

which compound of formula (IX) is subjected to catalytic hydrogenation conditions to yield a compound of formula (X):

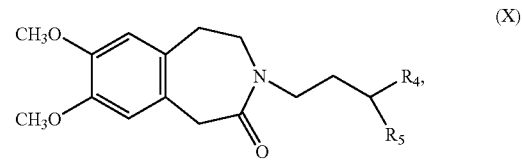

which compound of formula (X) is subjected to appropriate de rotection conditions to yield an aldehyde of formula (XI):

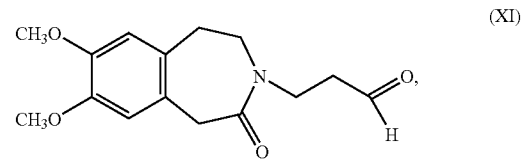

which compound of formula (XI) is reacted with (7S)-3,4-dimethoxybiclo [4.2.0.]octa-1,3,5-trien-7-yl]-N-methylmethanamine under conditions of reductive amination to yield ivabradine, which may optionally be converted into its addition salts with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

* * * * *

UNITED STATES PATENT AND TRADEMARK OFFICE
CERTIFICATE OF CORRECTION

| | |
|---|---|
| PATENT NO. | : 7,928,223 B2 |
| APPLICATION NO. | : 12/456437 |
| DATED | : April 19, 2011 |
| INVENTOR(S) | : Jean-Michel Lerestif et al. |

It is certified that error appears in the above-identified patent and that said Letters Patent is hereby corrected as shown below:

Column 12, Line 23: "de rotection" should be --deprotection--.

Signed and Sealed this
Fourteenth Day of June, 2011

David J. Kappos
*Director of the United States Patent and Trademark Office*